(12) United States Patent
Yacoubian

(10) Patent No.: US 10,687,869 B2
(45) Date of Patent: Jun. 23, 2020

(54) TROCHANTERIC NAIL WITH LOCKING OPENING

(75) Inventor: Stephen Yacoubian, Burbank, CA (US)

(73) Assignee: Advanced Orthopaedic Solutions, Inc., Torrance, CA (US)

( * ) Notice: Subject to any disclaimer, the term of this patent is extended or adjusted under 35 U.S.C. 154(b) by 2511 days.

(21) Appl. No.: 11/773,029

(22) Filed: Jul. 3, 2007

(65) Prior Publication Data

US 2008/0009873 A1    Jan. 10, 2008

Related U.S. Application Data

(60) Provisional application No. 60/818,734, filed on Jul. 5, 2006.

(51) Int. Cl.
*A61B 17/72* (2006.01)
*A61B 17/74* (2006.01)

(52) U.S. Cl.
CPC ............ *A61B 17/72* (2013.01); *A61B 17/744* (2013.01)

(58) Field of Classification Search
CPC ............................................. A61B 17/72–748
USPC ...................... 606/62–68, 87–89, 104, 96–98
See application file for complete search history.

(56) References Cited

U.S. PATENT DOCUMENTS

| | | | | |
|---|---|---|---|---|
| 3,670,724 A * | 6/1972 | Bosacco | ............ | A61B 17/1753 606/64 |
| 3,709,218 A * | 1/1973 | Halloran | ................ | A61B 17/72 606/64 |
| 4,103,683 A * | 8/1978 | Neufeld | ............... | A61B 17/744 606/64 |
| 4,622,959 A * | 11/1986 | Marcus | ........................... | 606/64 |
| 4,805,607 A * | 2/1989 | Engelhardt et al. | ............ | 606/67 |
| 4,978,349 A * | 12/1990 | Frigg | .................... | A61B 17/744 606/62 |
| 5,116,335 A * | 5/1992 | Hannon | .................. | A61B 17/72 606/62 |
| 5,176,681 A * | 1/1993 | Lawes | .................. | A61B 17/921 606/64 |
| 5,263,955 A * | 11/1993 | Baumgart et al. | ............... | 606/63 |
| 5,306,275 A * | 4/1994 | Bryan | ........................... | 606/914 |
| 5,312,406 A * | 5/1994 | Brumfield | .......... | A61B 17/1721 606/64 |
| 5,441,500 A * | 8/1995 | Seidel | ................ | A61B 17/7266 606/67 |
| 5,472,444 A * | 12/1995 | Huebner et al. | ................ | 606/64 |
| 5,514,137 A * | 5/1996 | Coutts | ................ | A61B 17/7098 606/62 |
| 5,549,610 A * | 8/1996 | Russell et al. | .................. | 606/64 |

(Continued)

*Primary Examiner* — Jacqueline T Johanas
(74) *Attorney, Agent, or Firm* — Burgess Law Office, PLLC

(57) ABSTRACT

A trochanteric nail for insertion in an intramedullary canal of a bone for treating bone fractures. The nail may include an elongate body having a head portion and a stem portion. One or more openings may be provided in the head portion for receiving an anchoring member, such as a bone screw, for fastening the nail within the bone. An intermediate opening may also be provided in the stem portion for receiving an anchoring member. A distal area of the nail may include or be free from anchoring members. In addition, a set of nails may be provided with each of the nails of the set of nails having different length in which the intermediate opening is the same distance from the proximal end for each of the nails.

5 Claims, 4 Drawing Sheets

(56) References Cited

U.S. PATENT DOCUMENTS

| | | | | |
|---|---|---|---|---|
| 5,562,667 | A * | 10/1996 | Shuler | A61B 17/7283 606/309 |
| 5,569,249 | A * | 10/1996 | James et al. | 606/62 |
| 5,620,445 | A * | 4/1997 | Brosnahan et al. | 606/63 |
| 5,766,174 | A * | 6/1998 | Perry | 606/62 |
| 5,855,579 | A * | 1/1999 | James et al. | 606/62 |
| 6,010,506 | A * | 1/2000 | Gosney | A61B 17/72 606/62 |
| 6,019,761 | A * | 2/2000 | Gustilo | A61B 17/72 606/62 |
| 6,123,708 | A * | 9/2000 | Kilpela | A61B 17/72 606/62 |
| 6,183,477 | B1 * | 2/2001 | Pepper | A61B 17/1725 606/104 |
| 6,210,414 | B1 * | 4/2001 | Lin | 606/64 |
| 6,224,601 | B1 * | 5/2001 | Friedl | 606/64 |
| 6,692,496 | B1 * | 2/2004 | Wardlaw | 606/64 |
| 6,730,090 | B2 * | 5/2004 | Orbay et al. | 606/62 |
| 2002/0183750 | A1 * | 12/2002 | Buhler | 606/62 |
| 2003/0004514 | A1 * | 1/2003 | Frigg et al. | 606/62 |
| 2003/0069581 | A1 * | 4/2003 | Stinson et al. | 606/62 |
| 2003/0149486 | A1 * | 8/2003 | Huebner | 623/19.11 |
| 2004/0082955 | A1 * | 4/2004 | Zirkle, Jr. | 606/62 |
| 2004/0172026 | A1 * | 9/2004 | Ekholm et al. | 606/62 |
| 2005/0096656 | A1 * | 5/2005 | Behrens | A61B 17/1721 606/64 |
| 2005/0182402 | A1 * | 8/2005 | Hansson | A61B 17/7233 606/64 |
| 2005/0187550 | A1 * | 8/2005 | Grusin | A61B 17/72 606/62 |
| 2005/0277936 | A1 * | 12/2005 | Siravo | A61B 17/72 606/62 |
| 2006/0084997 | A1 * | 4/2006 | Dejardin | A61B 17/1725 606/62 |
| 2006/0106386 | A1 * | 5/2006 | Reber | A61B 17/1721 606/65 |
| 2006/0111717 | A1 * | 5/2006 | Saueressig | A61B 17/72 606/64 |
| 2006/0122600 | A1 * | 6/2006 | Cole | A61B 17/164 606/62 |
| 2006/0200142 | A1 * | 9/2006 | Sohngen | A61B 17/72 606/62 |
| 2006/0293667 | A1 * | 12/2006 | Vignery | A61B 17/72 606/62 |
| 2007/0005146 | A1 * | 1/2007 | Heyligers | A61F 2/367 623/23.46 |
| 2007/0016203 | A1 * | 1/2007 | Schlienger et al. | 606/64 |
| 2007/0049939 | A1 * | 3/2007 | Wallace | A61B 17/744 606/62 |
| 2007/0100343 | A1 * | 5/2007 | Cole | A61B 17/72 606/67 |
| 2007/0173834 | A1 * | 7/2007 | Thakkar | A61B 17/7208 606/62 |
| 2007/0191855 | A1 * | 8/2007 | Orbay | A61B 17/1728 606/87 |
| 2007/0219636 | A1 * | 9/2007 | Thakkar | A61B 17/1721 623/18.11 |
| 2007/0233102 | A1 * | 10/2007 | Metzinger | A61B 17/744 606/62 |
| 2007/0276385 | A1 * | 11/2007 | Schlienger | A61B 17/72 606/71 |

* cited by examiner

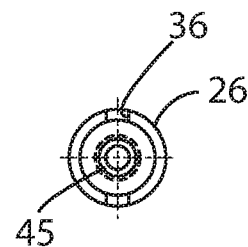
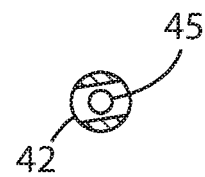
FIG. 7   FIG. 8
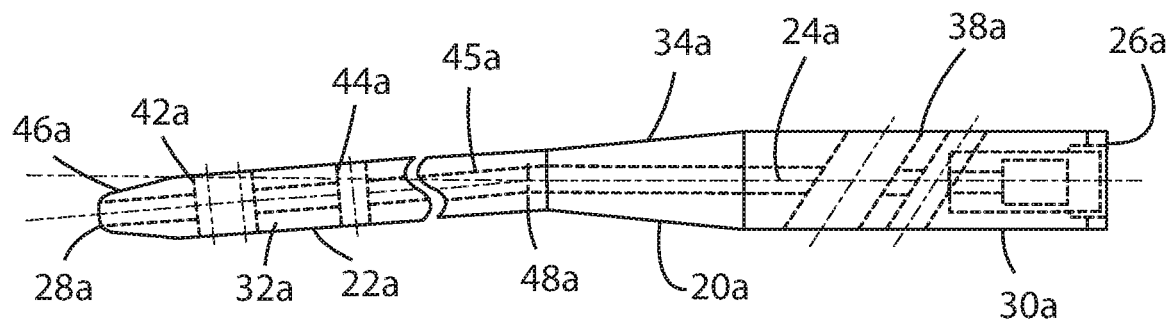
FIG. 11
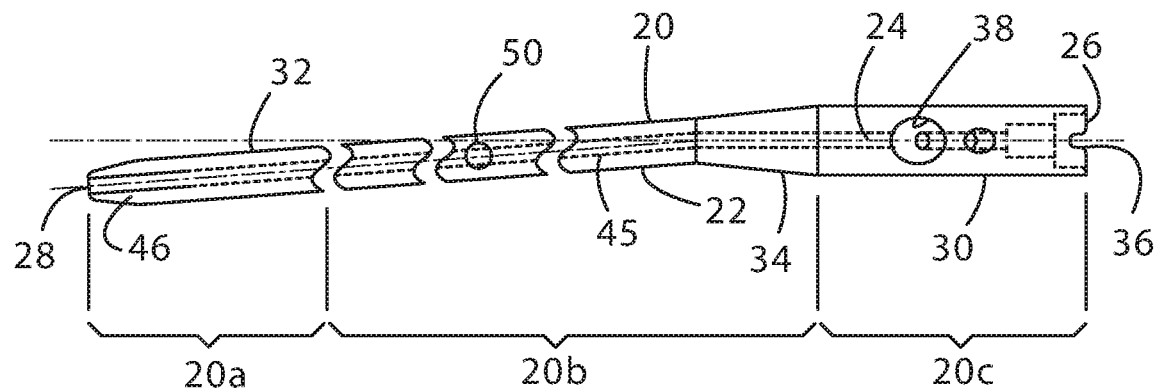
FIG. 12

TROCHANTERIC NAIL WITH LOCKING OPENING

CROSS-REFERENCE TO RELATED APPLICATIONS

This application claims the benefit of U.S. Provisional Application No. 60/818,734, filed Jul. 5, 2006.

STATEMENT REGARDING FEDERALLY SPONSORED RESEARCH OR DEVELOPMENT

Not Applicable.

BACKGROUND OF THE INVENTION

1. Field of the Invention

The present disclosure relates generally to bone treatment devices, and more particularly, but not necessarily entirely, to trochanteric nails for stabilizing bone fractures.

2. Description of Related Art

Intramedullary nails are proven devices that provide a temporary fixation means to stabilize a fracture until the fracture heals. The nail is inserted in the marrow canal of the bone and is positioned to span the fracture. The nail is anchored within the bone via bone screws placed through aligned apertures in the nail as received in the bone. The screws are usually inserted in the proximal and distal ends of the nail and the orientation of the screws depends upon the particular fracture configuration and the type of long bone fracture, i.e. femur, tibia, humerus.

Intramedullary nails may offer distinct advantages over other methods of fixation. For example, intramedullary nails may help bones heal faster, with lower rates of infection as compared to other surgical methods of fixation. Moreover, improved early mobilization of limbs having the broken bone may be achieved. One of the significant improvements over other methods of fixation is that intramedullary nails may share loads with the bone, rather that entirely supporting the bone across the fracture site. Because of this, patients may be able to move the broken limb sooner that they would with traditional casting of the bone. This may help maintain more strength of the muscles and prevent frozen joints, where joints become stiff after prolonged casting.

A drawback of some of the known intramedullary nails is that it may be difficult to install the bone screws into the apertures in the nail to fix the intramedullary nail in place. Surgeons are often required to place the bone screws through the apertures in the intramedullary nails, particularly apertures in the distal end of the nail, without the use of a guide jig.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

SUMMARY OF THE INVENTION

A trochanteric nail for insertion in an intramedullary canal of a bone for treating bone fractures. The nail may include an elongate body having a head portion at a proximal end and a stem portion toward a distal end. One or more openings may be provided in the head portion for receiving an anchoring member, such as a bone screw, for fastening the nail within the bone. An intermediate opening may also be provided in the stem portion for receiving an anchoring member. A distal area of the nail may be free from anchoring members. The nail may be provided as one of a set of nails having different lengths in which the intermediate opening is the same distance from the proximal end in each of the nails. Accordingly, a guide may be used to install the anchoring member in the intermediate opening.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features and advantages of the disclosure will become apparent from a consideration of the subsequent detailed description presented in connection with the accompanying drawings in which:

FIG. 7 is a proximal end view of the nail of FIG. 5;

FIG. 8 is a cross-sectional view of the nail of FIG. 5 taken along line 7-7;

FIG. 11 is a break-away top view of the left nail.

FIG. 12 is a break-away top view of an embodiment of the nail of FIG. 5 showing a bend in the nail with the distal area free of openings.

DETAILED DESCRIPTION OF THE PREFERRED EMBODIMENTS

Figure 1:
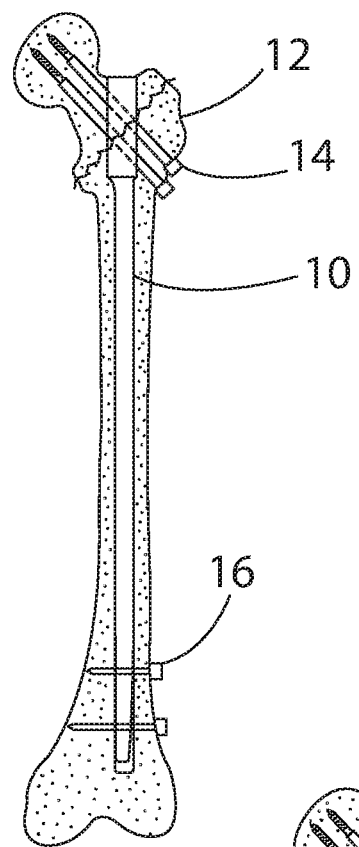
FIG. 1 is a schematic view of a known trochanteric nail of a long variety in a femur.

The following description of the preferred embodiment(s) is merely exemplary in nature and is in no way intended to limit the invention, its application, or uses.

For the purposes of promoting an understanding of these principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art having possession of this disclosure, are to be considered within the scope of the disclosure claimed.

Before the present apparatus and methods for treating a bone fracture are disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

It must be noted that, as used in this specification and the appended claims, the singular forms "a", "an", and "the" include plural referents unless the context clearly dictates otherwise. Moreover, as used herein, the terms "comprising", "including", "containing", "characterized by" and grammatical equivalents thereof are inclusive or open-ended terms that do not exclude additional, unrecited elements or method steps. In addition, the term "at" when referring to the location or placement of an element or object means in, near or by the area or location occupied by the particular structure or element referred to.

As used herein, the term "proximal" shall refer broadly to the concept of a nearest portion.

As used herein, the term "distal" shall generally refer to the opposite of proximal, and thus to the concept of a further portion, or a furthest portion, depending upon the context.

Referring now to FIG. 1, a schematic view is shown of a known trochanteric nail 10 in an intramedullary cavity of a femur 12. The nail 10 may be a relatively long variety, configured to extend a substantial entire length of the femur 12. One or more proximal anchoring members 14, such as bone screws, may be used to anchor a proximal end of the nail 10 within the femur 12, and one or more distal anchoring members 16 may be used to anchor a distal end of the nail 10.

Figure 2:
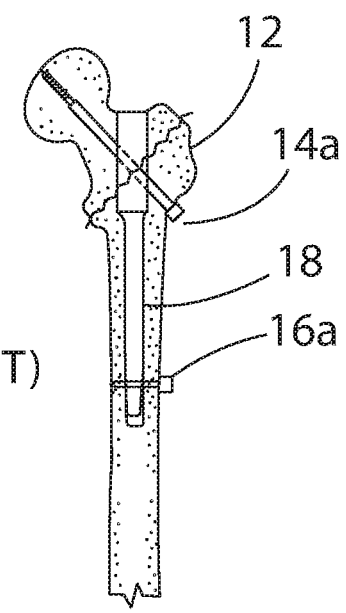
FIG. 2 is a schematic view of a known trochanteric nail of a short variety in a femur.

FIG. 2 shows a schematic view of another known trochanteric nail 18 in the intramedullary cavity of a femur 12. The nail 18 may be a relatively short variety, configured to extend only a partial length of the femur 12. One or more proximal anchoring members 14a, such as bone screws, may be used to anchor a proximal end of the nail 18 within the femur 12, and one or more distal anchoring members 16a may be used to anchor a distal end of the nail 18.

Figure 3:
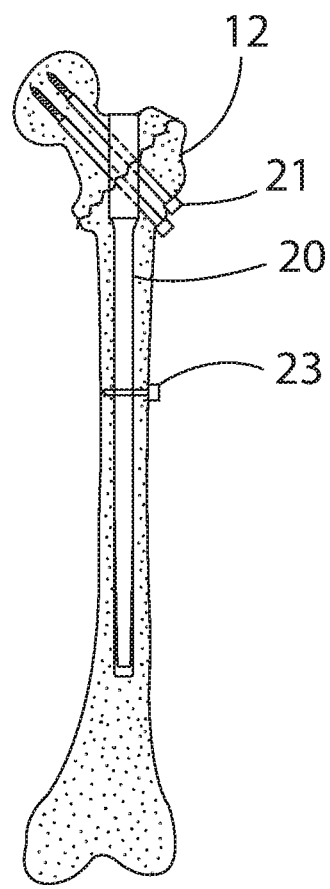
FIG. 3 is a schematic view of a trochanteric nail in a femur in accordance with the principles of the present disclosure.
Figure 4:
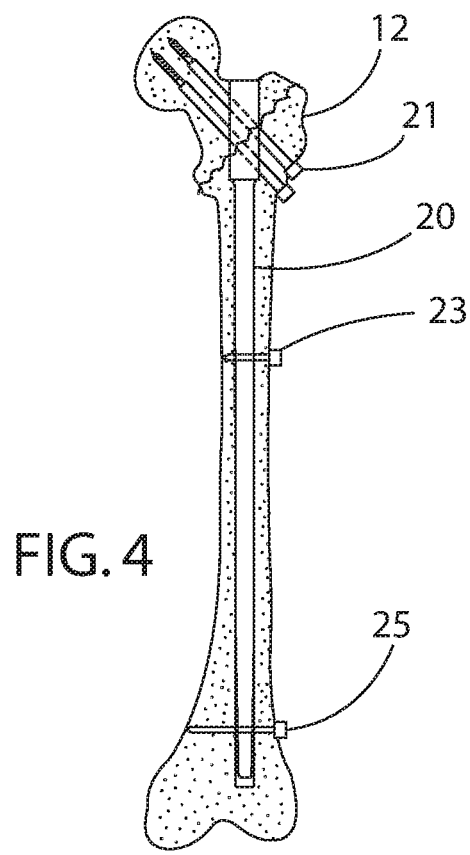
FIG. 4 is an alternative embodiment of a schematic view of a trochanteric nail in a femur in accordance with the principles of the present disclosure.

Referring now to FIGS. 3-4 schematic views are shown of a trochanteric nail 20 in accordance with the principles of the present disclosure. It is to be understood that the term "nail" as used here refers to a connective orthopedic nail implant, including but not limited to a trochanteric nail for use in a femur, as well as any other connective implant device suitable for use in any bone of interest. The nail 20 is depicted in the intramedullary cavity of a femur 12. It will be understood that the nail 20 may be useful in other types of bones in addition to femurs, in accordance with the principles of the present disclosure. It will be understood that an embodiment of the present disclosure may include the nail 20 configured to extend substantially an entire length of the bone. For example, as used herein, the phrase "substantial entire length" of a bone shall be construed to mean approximately seven-five percent of the length of the bone or more, for example, eighty percent of said length, or eight-five percent, or ninety percent, or ninety-five percent, or 99.9%, or any amount in between any of those. More specifically, one embodiment of the present disclosure may be configured to extend more that ninety percent of the length of the bone. It will be understood, however, that other embodiments of the nail may be configured to extend different lengths with respect to the bone.

One or more proximal anchoring members 21 may be used to anchor the nail 20 in the femur 12. It will be understood that the anchoring members 21 may be bone screws or any other suitable variety of fastening mechanism known in the art for use with trochanteric nails. Accordingly, the shape, size and configuration of the anchoring members 21 may vary within the scope of the present disclosure. In addition, as illustrated in FIG. 4, a distal anchoring member 25 can be used to anchor the nail 20 in the femur.

Figure 5:
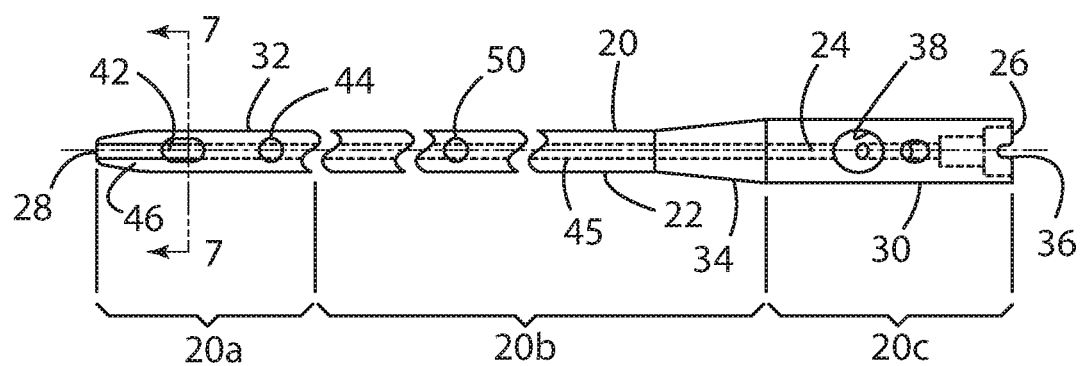
FIG. 5 is a break-away side view of one embodiment of a nail in accordance with the principles of the present disclosure.
Figure 6:
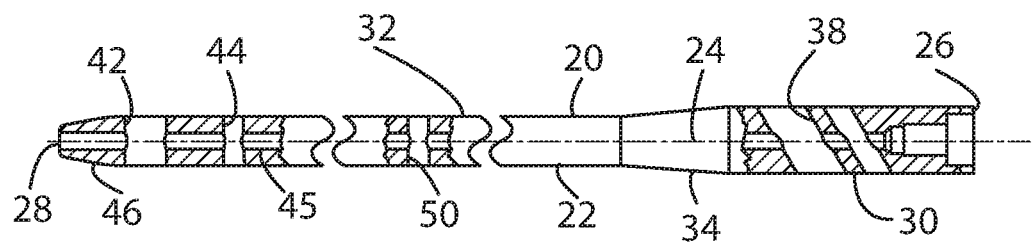
FIG. 6 is a break-away top view of the nail of FIG. 5 with portions of the nail shown in cross-section.
Figure 9:
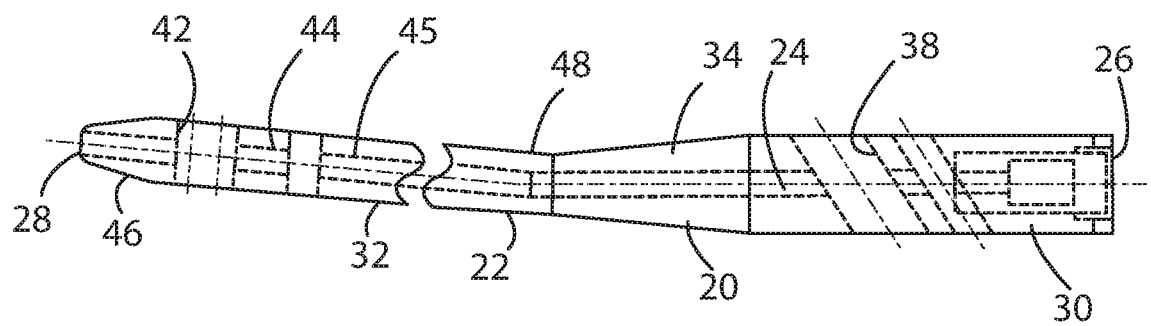
FIG. 9 is a break-away top view of the nail of FIG. 5 showing a bend in the nail.

Referring now to FIG. 5, a break-away side view is shown of one embodiment of the nail 20 in accordance with the principles of the present disclosure. The nail 20 may include an elongate body 22 having a longitudinal axis 24 extending between a proximal end 26 and a distal end 28. The body 22 may include a head portion 30 and a stem portion 32 located between the distal end 28 and a proximal end 26. With the head portion 30 being closer to the proximal end 26 and the stem portion 32 being closer to the distal end 28. The body 22 may also include a transition portion 34 between the head portion 30 and the stem portion 32. The transition portion 34 may include a cross-sectional taper from a larger diameter adjacent the head portion 30 to a smaller diameter adjacent the stem portion 32. Accordingly, the head portion 30 may include a diameter that may be larger that the stem portion 32.

The nail 20 may be viewed as including three areas or regions, a distal area 20a, a medial area 20b and a proximal area 20c. The distal area 20a is that area of the nail 20 located nearby or adjacent to the distal end 28. The proximal area 20c is that area of the nail 20 located nearby or adjacent to the proximal end 26. The medial area 20b is that area of the nail 20 located between the distal and proximal areas 20a, 20c. Typically, the stem portion 32 encompasses the medial area 20b and distal area 20a with the head portion 30 located in the proximal area 20c. In one embodiment, the areas are sized such that each of the respective areas 20a, 20b, 20c represents one-third (⅓) of the overall length of the elongate body 22. The size or length of the respective areas in relation to one another may vary depending upon the overall length of the elongate body 22 of the nail 20. For example, as the overall length of the elongate body 22 of the nail 20 increases, the overall increase in length typically occurs in the medial area 20b, whereby the medial area 20b may occupy more than one-half (½) of the overall length of the elongate body 22 of the nail 20.

A fitting 36 may be disposed on the head portion 30 at the proximal end 26. The fitting 36 may be configured for receiving a tool (not shown) for manipulating the nail 20, or for attaching an alignment guide or jig. The head portion 30 may also include one or more openings 38. The openings 38 extend across the longitudinal axis 24 for receiving anchoring members, such as bone screws, to anchor the nail 20 in a bone. The openings 38 extend across the longitudinal axis 24 at an angle of 90° or less.

The stem portion 32 may include a first opening 42 formed in the distal area 20a of the stem portion 32 near the distal end 28 in a direction transverse to the longitudinal axis 24. The first opening 42 may comprise an oblong cross-section to allow movement of an anchoring member 25 therein. A second opening 44 may also be formed in the distal area 20a near the distal end 28 of the body 22. The second opening 44 may include a round cross-sectional shape for receiving an anchoring member 25. While shown extending across the longitudinal axis 24 in a direction transverse the longitudinal axis 24, the openings 42, 44 may extend across the longitudinal axis 24 at an angle of 90° or less. It will be understood that other quantities of openings formed in the distal area 20a of the stem portion 32, or an embodiment may include no openings in the distal area 20a of the stem portion 32 remain within the scope of the present disclosure.

As disclosed herein, the stem portion 32 also includes an intermediate opening 50 located in the medial area 20b of the nail 20. The intermediate opening 50 is disposed between the distal end 28 and the head portion 30. The intermediate opening 50 configured for receiving an anchoring member 23. When the nail 20 includes openings in the distal area 20a, the intermediate opening 50 is spaced from and located between the openings and the head portion 30. As illustrated, the intermediate opening may also extend in a direction transverse to the longitudinal axis 24 or it may extend across the longitudinal axis 24 at an angle less than 90°. Accordingly, the nail 20 may be configured such that when the intermediate opening 50 receives an anchoring member, the distal area 20a of the nail 20 may remain free from anchoring members. For example, one embodiment of the nail may include a single intermediate opening 50 located in the stem portion 32 in an upper two-thirds (⅔) of the body 22, such that when an anchoring member is installed in the intermediate opening 50, a lower third (⅓) of the nail 20 remains free from an anchoring member. As used herein the term "upper" is associated with the proximal end 26 of nail 20 while "lower" is associated with the distal end 28.

Another embodiment may include a nail 20 having an intermediate opening 50 in the stem portion 32 in the upper one-half (½) portion of the body 22, such that when an anchoring member is installed in the intermediate opening 50, a lower one-half (½) of the nail 20 remains free from an anchoring member. Yet another embodiment may include a nail 20 having an intermediate opening 50 in the stem portion 32 in an upper one-third (⅓) of the body 22, such that when an anchoring member is installed in the intermediate opening 50, a lower two-thirds (⅔) of the nail 20 remains free from an anchoring member. Also, as illustrated in FIG. 4, another embodiment contemplates installing an anchor member in both the intermediate opening and at least one of the openings in the distal area.

One embodiment of the nail 20 may include a throughbore 45 extending from the proximal end 26 to the distal end 28 along the longitudinal axis 24. Also, a taper 46 may be positioned toward the distal end 28 of the stem portion 32. The taper 46 may facilitate insertion of the nail 20 in a bone canal. Moreover, one embodiment of the nail 20 may include a bend 48 (see FIG. 8) enabling the nail 20 to more closely align with a particular bone. However, it will be understood that some embodiments of the nail 20 may be provided with a bend in a different direction, as shown in FIG. 11 for example, and that other embodiments of the nail 20 may be provided without a bend.

One feature of the present disclosure may include a nail system for treating bone fractures in which the nail system includes a plurality of nails 20 having different lengths. Wherein the length is typically measured from the proximate end to the distal end. For example, the nails 20 may be provided in lengths of 30, 33, 36, 39, 42, and 48 centimeters. However, it will be understood that nails 20 of various different lengths may be utilized within the scope of the present disclosure. Each of the nails 20 may include an intermediate opening 50 spaced a uniform distance from the proximal end 26 such that the same targeting jig (not shown) may be used to install an anchoring member in the intermediate opening 50. This may be helpful in avoiding the requirement to install an anchoring member using the "freehand" method, wherein a surgeon installs the anchoring member without the assistance of an instrument such as a targeting jig. One embodiment of the present disclosure may include a plurality of nails 20 each having the intermediate opening 50 formed approximately 15.5 centimeters from the proximal end 26. It will be understood, however, that other embodiments may include the intermediate opening 50 positioned at different distances from the proximal end 26.

A feature of the present disclosure is that the nail 20 may be versatile for use in a traditional manner as shown in FIG. 1, in which distal anchoring members may be installed in the bone. Alternatively, the nail 20 may be used without anchoring members in the distal area 20a of the nail 20 as shown in FIG. 3.

In use, the nail 20 may be installed in the intramedullary canal of a bone, such as a femur 12. The nail 20 may extend a substantially entire length of the femur 12. One or more anchor members 21 may be installed in the openings 38 in the head portion 30. An anchor member 23 may be installed in the intermediate opening 50. It will be understood that a targeting jig may be used to position the anchor member 23 in the intermediate opening 50, since the intermediate opening 50 may be located closer to the proximal end 26 of the nail 20 than are the openings in the distal area 20a of some nails 20. The portion of the nail 20 from the intermediate opening 50 to the distal end 28 may remain free from anchoring members.

It will be appreciated that the nail 20 may be formed of any known material capable of providing suitable strength and durability characteristics, as well as allowing for compatibility with the bone in which it is to be installed.

Figure 10:
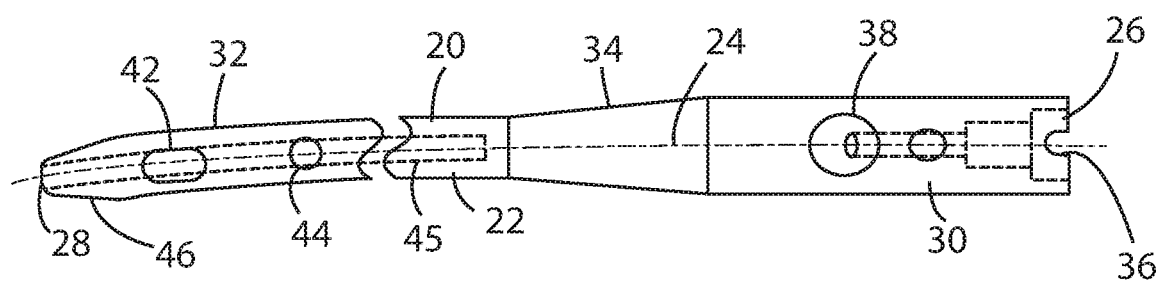
FIG. 10 is a break-away side view of the nail of FIG. 5 showing a bend in the nail.

Referring to FIG. 10, a break-away top view is shown of an alternative embodiment nail 20a. It will be understood that the nail 20a may be formed similar to the nail 20, except the nail 20a may be configured to be received in a different bone, such as a left femur. Accordingly, a bend 48a may be arranged to allow the nail 20a to correspond to a different bone.

Those having ordinary skill in the relevant art will appreciate the advantages provided by the features of the present disclosure. For example, it is a feature of the present disclosure to provide a trochanteric nail that is simple in design and manufacture. Another feature of the present disclosure is to provide such a trochanteric nail that may provide enhanced stability by filling substantially an entire bone canal. It is a further feature of the present disclosure, in accordance with one aspect thereof, to provide a nail that may be configured to reduce "pendulum" micro-motion and thereby reduce loosening of anchoring members. It is another feature of the present disclosure to provide a nail that may reduce the risk of bone fractures below the nail as may occur in instances where short nails are used. It is an additional feature of the present disclosure to provide a nail having an additional point of fixation that may be configured to span the isthmus of a bone canal. It is a further feature of the present disclosure to provide a nail with increased rigidity by decreasing the distance of the anchoring members from the proximal end of the nail. It is a further feature of the present disclosure to provide a nail that may allow a distal most anchoring member to be installed using a targeting jig rather than a freehand approach. It is another feature of the present disclosure to provide a nail that may allow a distal portion of the nail to be free from anchoring members. It is an additional feature of the present disclosure, to provide a nail system in which a plurality of nails are provided having different lengths, and an intermediate opening may be provided at a uniform distance from the proximal end such that anchoring members may be installed in the intermediate openings using the same targeting jig.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of treating a fracture in a bone includes the steps of:
    providing a plurality of nails with each nail having a different overall length, each nail having a proximal end, a distal end, a head portion and a stem portion, and a transition portion between the head portion and the stem portion, the head portion having an opening and the stem portion having an opening, each nail having a uniform distance from the proximal end to the opening in the stem portion;
    selecting a nail from the plurality of nails and inserting the nail into the bone;
    inserting a bone screw into the opening in the head portion;
    inserting a bone screw into the opening in the stem portion; and
    maintaining at least a lower third of the nail free from an anchoring member.

2. The method of treating a fracture in a bone as set forth in claim 1 including the step of maintaining a least a lower half of the nail free from an anchoring member.

3. The method of treating a fracture in a bone as set forth in claim 1 including the step of maintaining at least a lower two-thirds of the nail free from an anchoring member.

4. A nail system for treating a fracture in a bone comprising:
    a plurality of nails having different longitudinal lengths;
    each of said nails having an elongate body extending between a proximal end and a distal end, said body including a proximal area, a medial area and a distal area, a longitudinal axis extending between said proximal end located in said proximal area of said elongate body and said distal end located in said distal area of said elongate body, a head portion located in said proximal area and a stem portion located in said medial area and said distal area; said head portion having at least one opening extending transverse said longitudinal axis through said head portion and said stem portion free of openings in said distal area at said distal end; and
    said stem portion having an intermediate opening formed in said medial area wherein a distance from the proximal end to the intermediate opening is the same for each nail of the plurality of nails irrespective of the longitudinal length of each nail.

5. A nail for treating a fracture in a bone comprising:
    an elongate body configured to extend a substantial entire length of the bone, the elongate body having a longitudinal axis and extending between a proximal end and a distal end, wherein said elongate body includes a distal area, a medial area and a proximal area each of said distal area, medial area and proximal area representing one-third of the overall length of the elongate body;
    a head portion located in the proximal area, said head portion having a head diameter;
    a stem portion located in the distal area and the medial area, said stem portion having a stem diameter, wherein the head diameter is greater than the stem diameter;
    said stem portion having an intermediate opening in the medial area, said stem diameter adjacent said intermediate opening different than said head diameter, said intermediate opening extending transverse said longitudinal axis of said elongate body;
    a transition portion located adjacent said head portion;
    at least a lower half of the nail free from an opening for receiving an anchoring member; and
    said intermediate opening longitudinally spaced from said transition portion and adjacent said lower half of said nail.

* * * * *